US00PP35918P2

(12) United States Plant Patent
Yamada

(10) Patent No.: US PP35,918 P2
(45) Date of Patent: Jul. 2, 2024

(54) MANDEVILLA PLANT NAMED 'SUNPA 4351'

(50) Latin Name: *Mandevilla hybrida*
Varietal Denomination: Sunpa 4351

(71) Applicant: Masahiro Yamada, Shiga (JP)

(72) Inventor: Masahiro Yamada, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 18/372,931

(22) Filed: Sep. 26, 2023

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Mandevilla* plant named 'Sunpa 4351', characterized by its upright plant habit; vigorous growth habit; freely branching habit; early and freely flowering habit; long flowering period; and bluish purple-colored flowers.

2 Drawing Sheets

Figure 1:
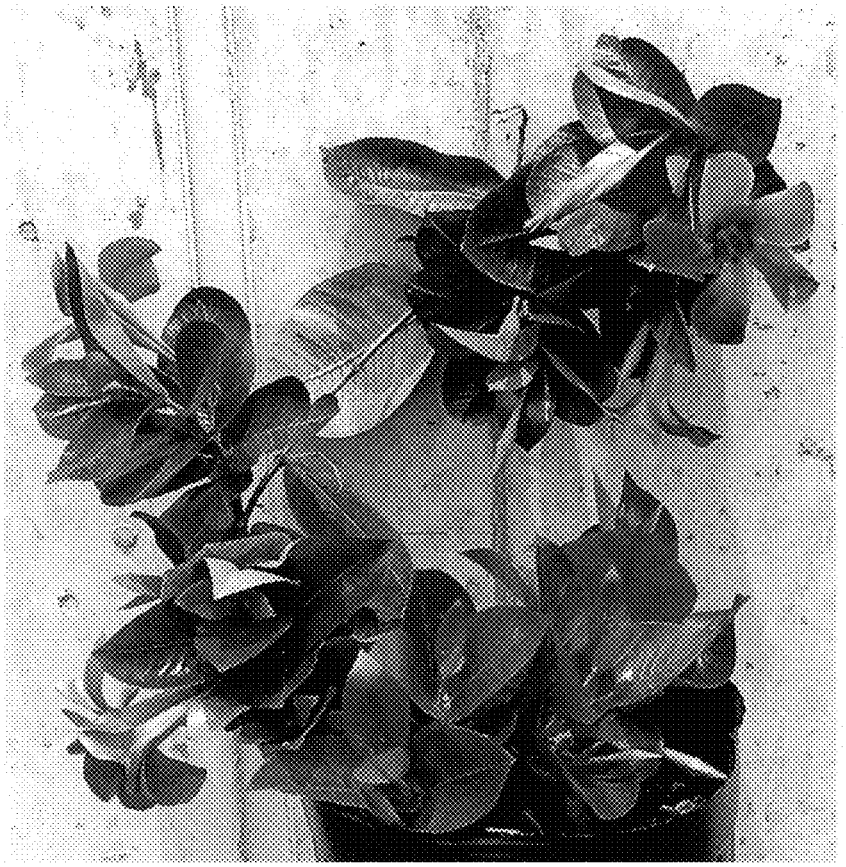

Botanical designation: *Mandevilla hybrida.*
Cultivar denomination: 'SUNPA 4351'.

BACKGROUND OF THE INVENTION

The present invention relates to a new and distinct cultivar of *Mandevilla* plant, botanically known as *Mandevilla hybrida* and hereinafter referred to by the name 'Sunpa 4351'.

The new *Mandevilla* plant is a product of a planned breeding program conducted by the Inventor in Higashiomi, Shiga, Japan. The objective of the breeding program is to create new upright and freely flowering *Mandevilla* plants with unique and attractive flower colors.

The new *Mandevilla* plant originated from a cross-pollination conducted by the Inventor in Higashiomi, Shiga, Japan in July, 2021 of a proprietary selection of *Mandevilla hybrida* identified as code number MW65, not patented, as the female, or seed parent with a proprietary selection of *Mandevilla hybrida* identified as code number MY15261, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in August, 2022.

Asexual reproduction of the new *Mandevilla* plant by terminal vegetative cuttings in Higashiomi, Shiga, Japan since December, 2022 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 4351'. These characteristics in combination distinguish 'Sunpa 4351' as a new and distinct *Mandevilla* plant:

1. Upright plant habit.
2. Vigorous growth habit.
3. Freely branching habit.
4. Early and freely flowering habit.
5. Long flowering period.
6. Bluish purple-colored flowers.

Plants of the new *Mandevilla* can be compared to plants of the female parent selection. Plants of the new *Mandevilla* differ primarily from plants of the female parent selection in flower color as plants of the new *Mandevilla* have bluish purple-colored flowers whereas plants of the female parent selection have pale blue-colored flowers. In addition, leaves of plants of the new *Mandevilla* are elliptic in shape whereas leaves of plants of the female parent selection are broadly elliptic to ovate in shape.

Plants of the new *Mandevilla* can be compared to plants of the male parent selection. Plants of the new *Mandevilla* differ primarily from plants of the male parent selection in flower color as plants of the new *Mandevilla* have bluish purple-colored flowers whereas plants of the male parent selection have reddish-colored flowers. In addition, leaves of plants of the new *Mandevilla* are elliptic in shape whereas leaves of plants of the male parent selection are broadly elliptic to ovate in shape.

Plants of the new *Mandevilla* can be compared to plants of the *Mandevilla hybrida* 'Sunpa 316', disclosed in U.S. Plant Pat. No. 31,236. In side-by-side comparisons, plants of the new *Mandevilla* differ from plants of 'Sunpa 316' in the following characteristics:

1. Plants of the new *Mandevilla* are shorter than plants of 'Sunpa 316'.

2. Leaves of plants of the new *Mandevilla* are longer and broader than leaves of plants of 'Sunpa 316'.
3. Plants of the new *Mandevilla* have bluish purple-colored flowers whereas plants of 'Sunpa 316' have bright red-colored flowers.
4. Plants of the new *Mandevilla* have shorter peduncles than plants of 'Sunpa 316'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Sunpa 4351' grown in a container.

Figure 2:
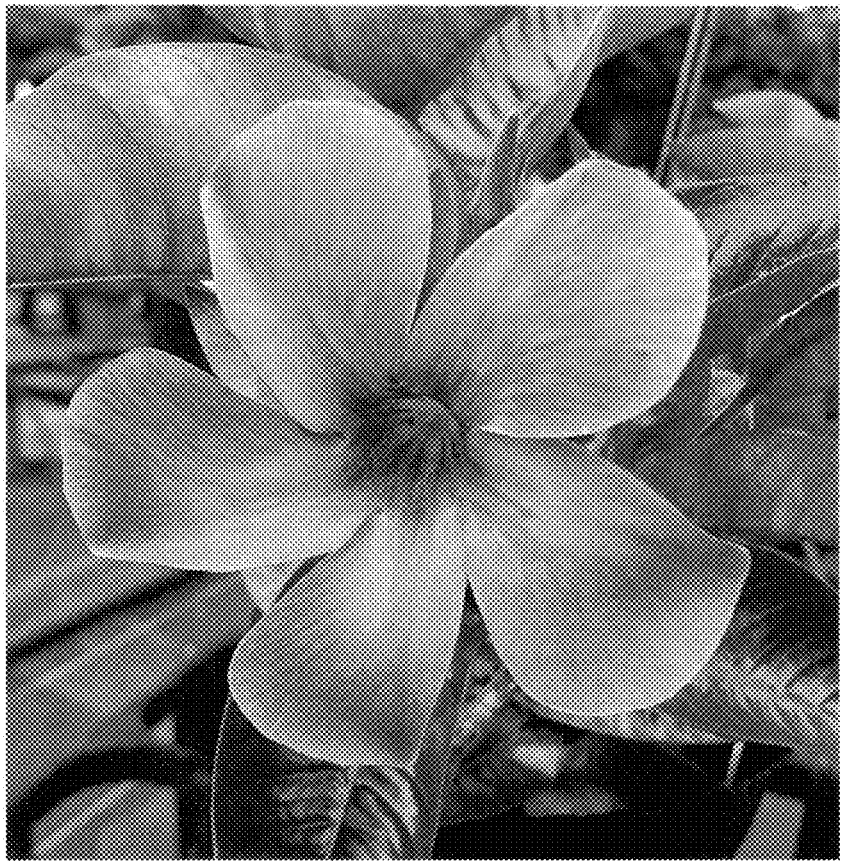

The photograph on the second sheet (FIG. 2) is a close-up view of a typical flower of 'Sunpa 4351'.

DETAILED BOTANICAL DESCRIPTION

The aforementioned photographs and following observations, measurements and values describe plants grown during the early summer in 15-cm containers in an outdoor nursery in Higashiomi, Shiga, Japan and under cultural practices typical of commercial *Mandevilla* production. During the production of the plants, day temperatures averaged 25 C and night temperatures averaged 15 C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 4351'.

Parentage:

*Female, or seed, parent*.—Proprietary selection of *Mandevilla hybrida* identified as code number MW65, not patented.

*Male, or pollen, parent*.—Proprietary selection of *Mandevilla hybrida* identified as code number MY15261, not patented.

Propagation:

*Type*.—By terminal vegetative cuttings.

*Time to initiate roots, summer and winter*.—About two weeks at temperatures about 23 C to 25 C.

*Time to produce a rooted young plant, summer and winter*.—About five to six weeks at temperatures about 23 C to 25 C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright plant habit; vigorous growth habit; freely branching habit; suitable for hanging baskets and garden plantings.

*Plant height*.—About 50 cm.

*Plant diameter*.—Variable.

*Lateral branch description*.—Length: About 41.4 cm. Diameter: About 3.3 mm. Internode length: About 4.6 cm. Strength: Strong, flexible. Texture: Pubescent; rough. Color, developing: Close to 138B. Color, fully developed: Close to N199C.

Leaf description:

*Arrangement and quantity*.—Decussate, simple; medium density, about 20 per lateral branch.

*Length*.—About 8.5 cm.

*Width*.—About 5.8 cm.

*Shape*.—Elliptic.

*Apex*.—Acuminate.

*Base*.—Rounded.

*Margin*.—Entire; slightly undulate.

*Texture and luster, upper and lower surfaces*.—Smooth, glabrous; moderately glossy.

*Venation pattern*.—Pinnate, reticulate.

*Color*.—Developing leaves, upper surface: Close to 138A. Developing leaves, lower surface: Close to 138B. Fully expanded leaves, upper surface: Close to 137A; venation, close to 137B. Fully expanded leaves, lower surface: Close to 137C; venation, close to 137D.

*Petioles*.—Length: About 3 mm. Diameter: About 3.1 mm. Texture, upper and lower surfaces: Sparsely pubescent; rough. Color, upper and lower surfaces: Close to 144B.

Flower description:

*Flower type and habit*.—Single salverform flowers; flowers face mostly outwardly; freely flowering habit with about four flowers per axil and typically about 24 flowers per plant.

*Natural flowering season*.—Early flowering habit, plants begin flowering about six weeks after planting rooted cuttings; long flowering period, plants flower continuously from summer until late autumn in Japan.

*Flower longevity on the plant*.—About seven to ten days; flowers not persistent.

*Fragrance*.—None detected.

*Flower buds*.—Height: About 5.5 cm. Diameter: About 8.7 mm. Shape: Trullate. Color: Proximally, close to 144B and distally, close to 64B and 64C.

*Flowers*.—Appearance: Salverform; flared trumpet, corolla fused and five-parted; flowers roughly star-shaped. Diameter: About 7.6 cm. Depth (length): About 6.5 cm. Throat diameter, distally: About 1.6 cm. Tube length: About 1.6 cm. Tube diameter, proximally: About 2.2 mm.

*Corolla*.—Quantity and arrangement: Five petals arranged in a single whorl and fused towards the base into an elongated tube; petal lobes slightly imbricate. Petal lobe length: About 3.6 cm. Petal lobe width: About 2.7 cm. Petal lobe shape: Spatulate, asymmetrical. Petal lobe apex: Obtuse. Petal lobe margin: Entire; slightly undulate and recurving. Petal lobe texture and luster, upper and lower surfaces: Smooth, glabrous; velvety; matte. Throat texture: Smooth, glabrous. Tube texture: Smooth, glabrous. Color: Petal lobe, when opening, upper surface: Close to 83B. Petal lobe, when opening, lower surface: Close to 83C and 64C. Petal lobe, fully opened, upper surface: Close to 83C and 84A; venation, similar to lamina colors; color does not change with subsequent development. Petal lobe, fully opened, lower surface: Close to 85A and 70B; venation, similar to lamina colors; color does not change with subsequent development. Throat: Proximally, close to 10A and distally, close to 84A; venation, close to N81B. Tube: Proximally, close to 185C and distally, close to 67C.

*Calyx*.—Quantity and arrangement: Five sepals arranged in a single whorl, fused at the base; calyx, star-shaped. Sepal length: About 2.1 mm. Sepal width: About 1.2 mm. Sepal shape: Lanceolate. Sepal apex: Acute. Sepal margin: Entire. Sepal texture, upper and lower surfaces: Smooth, glabrous. Sepal color, upper and lower surfaces: Close to 145C.

*Peduncles*.—Length: About 1.7 cm. Diameter: About 2.4 mm. Texture: Smooth, glabrous. Aspect: Upright to outwardly. Color: Close to 144A.

*Pedicels*.—Length: About 1.1 cm. Diameter: About 1.8 mm. Texture: Smooth, glabrous. Aspect: Upright to outwardly. Color: Close to 144B.

*Reproductive organs*.—Stamens: Quantity and arrangement: Typically five; filaments fused to corolla; anthers, connivent. Anther size: About 1.7 mm by 4.6 mm. Anther shape: Lanceolate. Anther color: Close to 2C. Pollen amount: Sparse. Pistils: Quantity: Typically one. Pistil length: About 2.2 cm. Style color: Close to 145B. Stigma shape: Globose. Stigma color: Close to 145A. Ovary color: Close to 145B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4 C to about 30 C.

It is claimed:

1. A new and distinct *Mandevilla* plant named 'Sunpa 4351' as illustrated and described.

* * * * *